(12) United States Patent
Jungong et al.

(10) Patent No.: US 11,999,673 B2
(45) Date of Patent: ***Jun. 4, 2024

(54) PROCESS FOR CATALYTIC CONVERSION OF MIXTURES OF HCFO-1233zd(Z) AND HCFC-244fa INTO HCFO-1233zd(E)

(71) Applicant: HONEYWELL INTERNATIONAL INC., Charlotte, NC (US)

(72) Inventors: Christian Jungong, Depew, NY (US); Daniel C. Merkel, Orchard Park, NY (US)

(73) Assignee: Honeywell International Inc., Charlotte, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/897,166

(22) Filed: Aug. 28, 2022

(65) Prior Publication Data

US 2022/0411354 A1 Dec. 29, 2022

Related U.S. Application Data

(63) Continuation of application No. 16/757,825, filed as application No. PCT/US2018/057469 on Oct. 25, (Continued)

(51) Int. Cl.
*C07C 17/358* (2006.01)
*C07C 17/25* (2006.01)
*C07C 17/383* (2006.01)

(52) U.S. Cl.
CPC ............ *C07C 17/358* (2013.01); *C07C 17/25* (2013.01); *C07C 17/383* (2013.01); *C07B 2200/09* (2013.01)

(58) Field of Classification Search
CPC .............................. C07C 17/358; C07C 17/25
See application file for complete search history.

(56) References Cited

U.S. PATENT DOCUMENTS

| 5,710,352 A | 1/1998 | Tung |
| 8,426,656 B2 * | 4/2013 | Merkel .................. C07C 17/25 570/166 |

(Continued)

FOREIGN PATENT DOCUMENTS

| CN | 102918010 A | 2/2013 |
| CN | 103429558 A | 12/2013 |

(Continued)

OTHER PUBLICATIONS

International Search Report and Written Opinion received for PCT Patent Application No. PCT/US2018/057469, dated Apr. 11, 2019, 8 pages.

*Primary Examiner* — Medhanit W Bahta
(74) *Attorney, Agent, or Firm* — Faegre Drinker Biddle & Reath LLP

(57) ABSTRACT

A method for conversion of a composition containing HCFO-1233zd(Z) and HCFC-244fa to form HCFO-1233zd(E) by reacting a mixture including HCFO-1233zd(Z) and HCFC-244fa in a vapor phase in the presence of a catalyst to simultaneously isomerize HCFC-1233zd(Z) to form HCFO-1233zd(E) and dehydrohalogenate HCFC-244fa to form HCFO-1233zd(E). The catalyst may be a chromium-based catalyst such as chromium trifluoride, chromium oxyfluoride, or chromium oxide, for example.

16 Claims, 1 Drawing Sheet

Related U.S. Application Data 2018, now Pat. No. 11,472,757, which is a continuation of application No. 15/794,562, filed on Oct. 26, 2017, now Pat. No. 10,118,879.

(56) References Cited

U.S. PATENT DOCUMENTS

| | | |
|---|---|---|
| 8,436,217 B2 * | 5/2013 | Wang .................... C07C 17/206 |
| | | 570/151 |
| 10,118,879 B1 | 11/2018 | Jungong et al. |
| 11,472,757 B2 | 10/2022 | Jungong et al. |
| 2011/0245549 A1 | 10/2011 | Merkel et al. |
| 2012/0059200 A1 | 3/2012 | Pokrovski et al. |
| 2012/0172636 A1 | 7/2012 | Pokrovski et al. |
| 2012/0184786 A1 | 7/2012 | Merkel et al. |
| 2012/0271070 A1 | 10/2012 | Wang et al. |
| 2021/0188744 A1 | 6/2021 | Jungong et al. |

FOREIGN PATENT DOCUMENTS

| | | |
|---|---|---|
| CN | 103476736 A | 12/2013 |
| EP | 2112131 A1 | 10/2009 |
| JP | 2013-523812 A | 6/2013 |
| JP | 2014-525893 A | 10/2014 |
| WO | 2016/111227 A1 | 7/2016 |

* cited by examiner

PROCESS FOR CATALYTIC CONVERSION OF MIXTURES OF HCFO-1233zd(Z) AND HCFC-244fa INTO HCFO-1233zd(E)

CROSS-REFERENCE TO RELATED APPLICATIONS

This application is a continuation of U.S. patent application Ser. No. 16/757,825, filed Apr. 21, 2020, which is a U.S. 371 Application of International Application No. PCT/US2018/057469, filed Oct. 25, 2018, which is a continuation of U.S. patent application Ser. No. 15/794,562, filed Oct. 26, 2017, issued as U.S. Pat. No. 10,118,879 on Nov. 6, 2018, all of which are herein incorporated by reference in their entireties.

BACKGROUND

1. Field of the Disclosure

The present disclosure relates to a process for the catalytic conversion of mixtures of (Z)-1-chloro-3,3,3-trifluoropropene (HCFO-1233zd(Z), or 1233zd(Z)) and 1-chloro-1,3,3,3-tetrafluoropropane (HCFC-244fa, or 244fa) to (E)-1-chloro-3,3,3-trifluoropropene (HCFO-1233zd(E), or 1233zd(E)).

2. Description of the Related Art (E)-1-chloro-3,3,3-trifluoropropene (HCFO-1233zd(E), or 1233zd(E)) is a new Low Global Warming and Non-Ozone Depleting molecule, which has applications as a blowing agent, solvent, and refrigerant. The applications and interest in this molecule resulted in the development of several manufacturing processes for its production. On a commercial scale, HCFO-1233zd(E) is produced by fluorination of 1,1,1,3,3-pentachloropropane (HCC-240fa) using hydrofluoric acid (HF), in which (Z)-1-chloro-3,3,3-trifluoropropene (HCFO-1233zd(Z), or 1233zd(Z)) is produced as a by-product in about a 10-20:1 ratio of HCFO-1233zd(E) to HCFO-1233zd(Z), alongside about 2-10 wt. % of 1-chloro-1,3,3,3-tetrafluoropropane (HCFC-244fa, or 244fa). Disadvantageously, the formation of HCFO-1233zd(Z) and HCFC 244fa results in yield losses.

Due to the fact that HCFO-1233zd(Z) and HCFC-244fa have similar boiling points and corresponding mixtures of these compounds exhibit azeotrope-like properties, these two components cannot be separated by conventional distillation techniques. Also, although HCFO-1233zd(Z) has application as an alternative higher-boiling solvent, HCFC-244fa is especially toxic, making it impossible for mixtures of these compounds to be stored for extended periods. As a result, mixtures of HCFC-244fa and HCFO-1233zd(Z) resulting from the commercial production of HCFO-1233zd(E) are typically transported to a thermal oxidizer for destruction, incurring further manufacturing costs.

Therefore, there is increasing need to develop a productive use for mixtures of HCFC-244fa and HCFO-1233zd(Z) in order to reduce waste, improve overall yield, and reducing manufacturing costs.

SUMMARY

The present disclosure provides a method for conversion of a composition containing HCFO-1233zd(Z) and HCFC-244fa to form HCFO-1233zd(E) by reacting a mixture including HCFO-1233zd(Z) and HCFC-244fa in a vapor phase in the presence of a catalyst to simultaneously isomerize HCFO-1233zd(Z) to form HCFO-1233zd(E) and dehydrohalogenate HCFC-244fa to form HCFO-1233zd(E). The catalyst may be a chromium-based catalyst such as chromium trifluoride, chromium oxyfluoride, or chromium oxide, for example.

In one form thereof, the present invention provides a method for the simultaneous conversion of a composition containing HCFO-1233zd(Z) and HCFC-244fa to form HCFO-1233zd(E), including the steps of: providing a composition including HCFO-1233zd(Z) and HCFC-244fa; and reacting the composition in a vapor phase in a reactor in the presence of a chromium trifluoride ($CrF_3$) catalyst to simultaneously isomerize HCFO-1233zd(Z) to form HCFO-1233zd(E) and dehydrohalogenate HCFC-244fa to form HCFO-1233zd(E).

The reacting step may be conducted at a temperature between 80° C. and 250° C., or between 100° C. and 200° C. A contact time between the composition and the catalyst may be between 1 second and 150 seconds, or may be between 25 seconds and 125 seconds. A pressure in the reactor may be between 25 psig and 100 psig.

During the reacting step, the reactor may include less than 50 ppm water. The reacting step may achieve a conversion of HCFO-1233zd(Z) to HCFO-1233zd(E) between 88% and 96%, may achieve a conversion of HCFC-244fa to HCFO-1233zd(E) between 90% and 99%, and/or may achieve a selectivity to HCFO-1233zd(E) between 90% and 97%.

In the providing step, total impurities may be present in an amount less than 10 wt. %, based on the total weight of the composition, may be present in an amount less than 6 wt. %, based on the total weight of the composition, or may be present in an amount less than 1.5 wt. %, based on the total weight of the composition. Any HCFC-243fa and HCFC-243db, if present in the composition, may be present in an amount less than 3 wt. % based on the total weight of the composition.

After the reacting step, the method may include the additional steps of: distilling the composition in a distillation column; removing an overhead stream from the distillation column, the overhead stream concentrated in HCFO-1233zd (E); and removing a bottoms stream from the distillation column, the bottoms stream concentrated in HCFO-1233zd (Z) and HCFC-244fa. The method may further include, after the second removing step, the additional step of recycling the bottoms stream back to the reactor.

BRIEF DESCRIPTION OF THE DRAWINGS

The above mentioned and other features of the disclosure, and the manner of attaining them, will become more apparent and the disclosure itself will be better understood by reference to the following description of embodiments of the disclosure taken in conjunction with the accompanying drawings.

Figure 1:
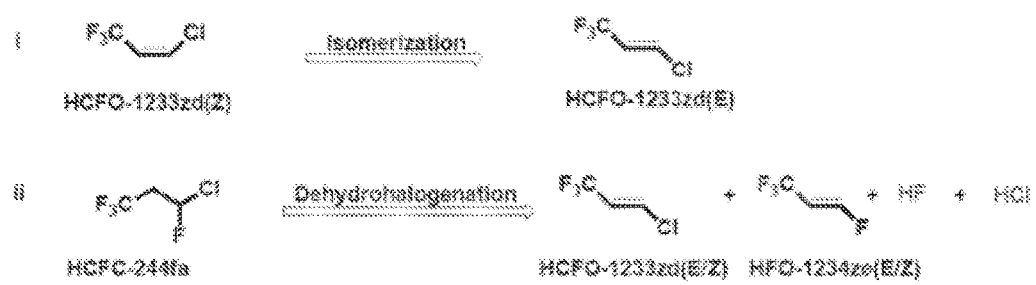
FIG. 1 shows the following reactions: (i) isomerization of HCFO-1233zd(Z) to form HCFO-1233zd(E) and (ii) dehydrohalogenation of HCFC-244fa to form HCFO-1233zd(E), hydrogen fluoride, and hydrogen chloride.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplification set out herein illustrates an embodiment of the disclosure, and such exemplification is not to be construed as limiting the scope of the disclosure in any manner.

DETAILED DESCRIPTION

The present disclosure provides a method for conversion of a composition containing HCFO-1233zd(Z) and HCFC-244fa to form HCFO-1233zd(E) by reacting a mixture including HCFO-1233zd(Z) and HCFC-244fa in a vapor phase in the presence of a catalyst to simultaneously isomerize HCFO-1233zd(Z) to form HCFO-1233zd(E) and dehydrohalogenate HCFC-244fa to form HCFO-1233zd(E). The catalyst may be a chromium-based catalyst such as chromium trifluoride, chromium oxyfluoride, or chromium oxide, for example.

Referring to FIG. 1, isomerization of HCFO-1233zd(Z) (i.e., cis-HCFO-1233zd, or c-1233zd) to form HCFO-1233zd(E) (i.e., trans-HCFO-1233zd or t-1233zd) is shown in reaction (i), and dehydrohalogenation of HCFC-244fa to form HCFO-1233zd(E), hydrogen fluoride, and hydrogen chloride is shown in reaction (ii). According to the present disclosure, is has been found that both of the foregoing reactions may be carried out simultaneously using the same catalyst. Specifically, the present disclosure introduces a manufacturing process that converts mixtures of HCFO-1233zd(Z) and HCFC-244fa into HCFO-1233zd(E) by heterogeneous vapor phase catalysis.

Figure 2:
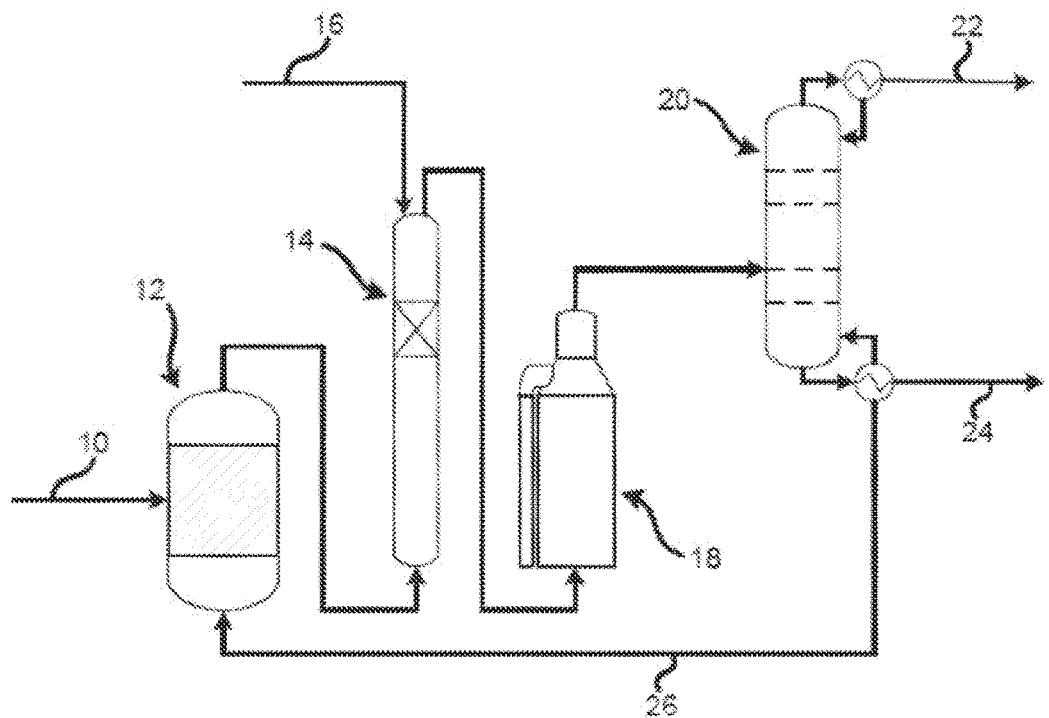
FIG. 2 is a process schematic for carrying out the reactions of FIG. 1.

A process schematic for carrying out the present reaction is shown in FIG. 2. An input stream 10 which includes HCFO-1233zd(Z) and HCFC-244fa is provided to reactor 12. The HCFO-1233zd(Z) and HCFC-244fa in input stream 10 may be present in any desired amounts, both relative to one another and/or to the total weight of the overall mixture though, as described below, for avoidance of formation of certain by-products, it may be desirable to limit the total amount of HCFC-244fa in input stream 10.

Input stream 10 may itself be a distillation fraction obtained from a commercial production process for preparing HCFO-1233zd(E). In this connection, input stream 10 may also include HCFO-1233zd(E) in any amount, which will not affect the conversion of the HCFO-1233zd(Z) and HCFC-244fa present within input stream 10 to HCFO-1233zd(E). Alternatively, input stream 10 may be a recycle stream from the distillation column described below, which includes unreacted HCFO-1233zd(Z) and HCFC-244fa. Input stream 10 may also be a combination of the foregoing.

Input stream 10 may also include minor amounts of other impurities, such as HCFC-243fa and HCFC-243db, for example, wherein it has been found that the presence of HCFC-243fa and HCFC-243db in amounts of less than 3 wt. % in the mixtures of HCFO-1233zd(Z) and HCFC-244fa, based on the total weight of the composition of stream 10 have little or no significant effect on the product distribution.

The total amount of impurities in input stream 10, specifically, all compounds other than HCFO-1233zd(Z), HCFC-244fa, and HCFO-1233zd(E), in input stream 10, may be less than 10 wt. %, less than 8 wt. %, less than 6 wt. %, or even less than 1.5 wt. %, based on the total weight of the all of the compounds in input stream, wherein higher concentrations of impurities may potentially result in loss of catalyst activity over time, such that higher amounts of impurities are not desirable for extended operating periods.

In reactor 12, the HCFO-1233zd(Z) and HCFC-244fa are vaporized and reacted in the vapor phase in the presence of a catalyst, such as a heterogeneous catalyst which, in the present reaction, will be a solid catalyst.

Suitable chromium-based catalysts include chromium oxides, chromium oxyfluorides, and chromium halides. The chromium oxides may include amorphous chromium oxide ($Cr_2O_3$), crystalline chromium oxide, and combinations of the foregoing. The chromium oxyfluorides may include fresh amorphous chromium oxide ($Cr_2O_3$) pretreated with HF, fresh crystalline chromium oxide ($Cr_2O_3$) pretreated with HF, amorphous chromium oxyfluoride ($Cr_xO_yF_z$, where x may be 1 or 2, y may be 1 or 2, and z may be 1, 2, or 4), crystalline chromium oxyfluoride ($Cr_xO_yF_z$, where x may be 1 or 2, y may be 1 or 2, and z may be 1, 2, or 4), and combinations of the foregoing. In one embodiment, the catalyst is amorphous chromium oxyfluoride ($Cr_xO_yF_z$, where x may be 1 or 2, y may be 1 or 2, and z may be 1, 2, or 4). The chromium halides may include chromium trifluoride ($CrF_3$), chromium trichloride ($CrCl_3$), chromium triiodide ($CrI_3$) and chromium tribromide ($CrBr_3$), and combinations of the foregoing. In one embodiment, the catalyst is chromium trifluoride ($CrF_3$).

In addition to chromium-based catalysts, other suitable catalysts include other metal halides, such as nickel fluorides, titanium fluorides, molybdenum fluorides, cobalt fluorides, aluminum fluoride, and combinations of the foregoing.

Suitable reaction temperatures in reactor 12 may be as little as 100° C., 125° C., 150° C., 175° C., or as great as 200° C., 225° C., 250° C., or 275° C., or within any range defined between any pair of the foregoing values, such as from 100° C. to 275° C., from 125° C. to 250° C., from 150° C. to 225° C., or from 175° C. to 200° C., for example.

Advantageously, when chromium trifluoride ($CrF_3$) is used as the catalyst, the present simultaneous isomerization and dehydrohalogenation reactions may be carried out to achieve effective conversion and selectivity at relatively low temperatures, such as 80° C., 100° C., or 125° C., or as great as 175° C., 200° C., or 250° C., or within any range defined between any pair of the foregoing values, such as from 80° C. to 250° C., from 100° C. to 200° C., or from 125° C. to 175° C., for example.

Suitable reaction pressures in reactor 12 may be as little as 0, psig, 25 psig, 50 psig, or 75 psig, or as great as 100 psig, 125 psig, or 150 psig, or within any range defined between any pair of the foregoing values, such as from 0 psig to 150 psig, from 25 psig to 125 psig, or from 50 psig to 100 psig, for example. In one embodiment, the reaction pressure in the reactor is about 50 psig.

The amount of catalyst used may vary, but generally the contact time between stream 10 and the catalyst in reactor 12 may be as little as 1 second, 25 seconds, or 50 seconds, or as great as 100 seconds, 125 seconds, or 150 seconds, or within any range defined between any pair of the foregoing values, such as from 1 second to 150 seconds, from 25 seconds to 125 seconds, or from 50 seconds to 100 seconds, for example.

The presence of water or water vapor within reactor 12 may have a detrimental impact on the chromium-based catalysts, potentially leading to rapid catalyst deactivation. Therefore, the input stream and/or mixture in reactor 12 may include less than 0.0050 wt. % (50 ppm) water, less than 0.0030 wt. % (30 ppm) water, or less than 0.0020 wt. % (20 ppm) water, for example.

One by-product that may be produced during the simultaneous isomerization and dehydrohalogenation of HCFO-1233zd(Z) and HCFC-244fa, respectively, to form HCFO-1233zd(E), is 1,1,1,3,3-pentafluoropropane (HFC-245fa).

The formation of HFC-245fa results in yield losses due to the potential formation of a binary azeotrope between HCFO-1233zd(E) and HFC-245fa. However, it has been found that selectivity to the undesired by-product HFC-245fa may be limited to under 5% when the reaction mixture includes less than 15 wt. % HCFC-244fa.

In addition to HFC-245fa, hydrofluoric acid and hydrochloric acid are generated from the dehydrohalogenation reaction of HCFC-244fa. Referring to FIG. 2, these acids generated during the reaction may be neutralized without impacting product and by-product distribution by passing the product stream through a caustic scrubber 14 using a 10 wt. % sodium hydroxide in water solution 16, for example, though other caustic (basic) solutions of other concentrations may also be used. After passing through caustic scrubber 14, the composition may be passed through a drier 18 including a suitable drying agent to remove moisture.

In addition to HFC-245fa, other by-products may include HCFC-243fa and both isomers of 1,3,3,3-tetrafluoropropene (HFO-1234ze(Z) and HFO-1234ze(E)). As shown in FIG. 2, except for HFC-245fa, which may potentially form a binary azeotrope with HCFO-1233zd(E), all other by-products may be easily separated from the HCFO-1233zd(E) product by conventional distillation using distillation column 20, in which by-products are removed in either overhead stream 22 or bottoms stream 24, depending on their boiling point.

The HCFO-1233zd(E) product will be concentrated in overhead stream 22, meaning that more HCFO-1233zd(E) product is present in overhead stream 22 than in bottoms stream 24, and any remaining unreacted HCFO-1233zd(Z) and HCFC-244fa will be concentrated in bottoms stream 24, meaning that more HCFO-1233zd(Z) and HCFC-244fa is present in bottoms stream 24 than in overhead stream 22. Optionally, the unreacted HCFO-1233zd(Z) and HCFC-244fa may be returned to reactor 12 via recycle stream 26.

Advantageously, in the present process, conversion of HCFO-1233zd(Z) to HCFO-1233zd(E), during simultaneous isomerization of HCFO-1233zd(Z) and dehydrohalogenation of HCFC-244fa, may be higher than 88%, higher than 90%, higher than 93%, higher than 95%, up to 96%, and conversion of HCFC-244fa to HCFO-1233zd(E), during simultaneous isomerization of HCFO-1233zd(Z) and dehydrohalogenation of HCFC-244fa, may be higher than 99%, 90%, higher than 92% higher than 95%, higher than 97%, and up to 96% or 99%.

Also, in the present process, selectivity to HCFO-1233zd (E) based on simultaneous isomerization of HCFO-1233zd (Z) and dehydrohalogenation of HCFC-244fa may be higher than 90%, higher than 92%, higher than 95%, higher than 96%, up to 97%.

EXAMPLE 1

Simultaneous Isomerization and Dehydrohalogenation Using $CrF_3$ Catalyst

A feed stream consisting of HCFO-1233zd(Z), HCFC-244fa, and HCFO-1233zd(E) was vaporized and reacted in the vapor phase over $CrF_3$ catalyst to produce HCFO-1233zd(E). Specifically, the feed material consisting of about 77 GC area % HCFO-1233zd(Z), 7.97 GC area % HCFC-244fa, and 13.89 GC area % HCFO-1233zd(E) was vaporized and fed to a 1 inch reactor containing 0.28 L of $CrF_3$ pellets, at a rate of 0.3 lb/hr (136 g/hr), and reactor pressure of 50 psig. The reaction temperature was varied from 100-220° C. The average productivity observed was 27,725 lb/hr (1.26 kg/hr) of HCFO-1233zd(E) per cubic foot (0.028 cubic meter) of $CrF_3$ catalyst. Table 1 shows average conversions of HCFO-1233zd(Z) and HCFC-244fa, and average selectivity to HCFO-1233zd(E) and byproducts, as a function of temperature using $CrF_3$ catalyst.

TABLE 1

Average conversions of HCFO-1233zd(Z) and HCFC-244fa, and average selectivities to HCFO-1233zd(E) and byproducts using $CrF_3$ catalyst

| | Avg. Conversion (%) | | Avg. Selectivity (%) | | | | | |
|---|---|---|---|---|---|---|---|---|
| T, ° C. | c-1233zd | 244fa | t-1234ze | 245fa | c-1234ze | t-1233zd | 243fa | others |
| 220 | 91.628 | 95.614 | 0.976 | 2.667 | 0.193 | 95.631 | 0.394 | 0.138 |
| 150 | 94.209 | 89.993 | 0.244 | 3.220 | 0.022 | 95.761 | 0.695 | 0.057 |
| 100 | 95.145 | 88.467 | 0.112 | 3.446 | 0.002 | 96.016 | 0.386 | 0.039 |

Other reaction conditions: 50 psig; 0.3 lb/hr; 0.28 L $CrF_3$; feed composition: 77.98% HCFO-1233zd(Z), 14.29% HCFO-1233zd(E), 7.42% HCFC-244fa, & 0.31% others; each temperature was run for at least 24 h; Productivity: 27.725 lb/hr/ft$^3$

EXAMPLE 2

Simultaneous Isomerization and Dehydrohalogenation Using Amorphous Chromium Oxyfluoride Catalyst A feed stream consisting of HCFO-1233zd(Z), HCFC-244fa, and HCFO-1233zd(E) was vaporized and reacted in the vapor phase over amorphous chromium oxyfluoride catalyst to produce HCFO-1233zd(E). Specifically, the feed material consisting of about 91.70 GC area % HCFO-1233zd(Z), 7.99 GC area % HCFC-244fa, and 0.278 GC area % HCFO-1233zd(E) was vaporized and fed to a 1 inch reactor containing 0.28 L of amorphous chromium oxyfluoride pellets, at a rate of 0.3 lb/hr (136 g/hr), and reactor pressure of 50 psig. The reaction temperature was varied from 125-275° C. The average productivity observed was 24.7 lb/hr (11.21 kg/hr) of HCFO-1233zd(E) per cubic foot (0.028 cubic meter) of amorphous chromium oxyfluoride catalyst. Table 2 shows average conversions of HCFO-1233zd(Z) and HCFC-244fa, and average selectivity to HCFO-1233zd(E) and byproducts, as a function of temperature using amorphous chromium oxyfluoride catalyst.

TABLE 2

Average conversions of HCFO-1233zd(Z) and HCFC-244fa, and average selectivities to HCFO-1233zd(E) and byproducts using amorphous chromium oxyfluoride catalyst

| | Avg. Conversion, % | | Avg. Selectivity, % | | | | | |
|---|---|---|---|---|---|---|---|---|
| T, C. | c-1233zd | 244fa | t-1234ze | 245fa | c-1234ze | t-1233zd | 243fa | Others |
| 125 | 92.8934 | 89.8086 | 0.3626 | 4.9894 | 0.0398 | 93.1119 | 1.4793 | 0.0170 |
| 150 | 91.2908 | 91.6583 | 0.8702 | 3.8527 | 0.1200 | 94.5694 | 0.5503 | 0.0374 |
| 175 | 92.6914 | 95.4055 | 1.3501 | 3.4827 | 0.1954 | 94.6196 | 0.3130 | 0.0392 |
| 188 | 91.6803 | 97.8617 | 2.3461 | 3.0495 | 0.4084 | 94.0034 | 0.1358 | 0.0569 |
| 200 | 91.7271 | 97.1831 | 2.4602 | 2.4881 | 0.4166 | 94.4541 | 0.1314 | 0.0497 |
| 200 | 90.9592 | 97.9183 | 2.3177 | 2.6524 | 0.4330 | 94.3907 | 0.1319 | 0.0743 |
| 212 | 90.3545 | 98.3907 | 3.0319 | 1.9764 | 0.5976 | 94.2306 | 0.0802 | 0.0834 |
| 225 | 90.7836 | 98.0652 | 3.1877 | 1.7736 | 0.6004 | 94.2663 | 0.0791 | 0.0930 |
| 225 | 89.4564 | 98.7789 | 3.8874 | 1.3065 | 0.8304 | 93.8267 | 0.0416 | 0.1073 |
| 237 | 89.5061 | 99.2996 | 4.7924 | 0.9233 | 1.0471 | 93.0456 | 0.0504 | 0.1412 |
| 250 | 91.1685 | 98.4887 | 3.9472 | 1.6605 | 0.7183 | 93.5373 | 0.0439 | 0.0927 |
| 275 | 88.4857 | 99.4017 | 5.2453 | 0.6503 | 1.1931 | 92.5230 | 0.0561 | 0.3322 |

Other reaction conditions: 50 psig; 0.3 lb/hr; 0.28 L amorphous chromium oxyfluoride catalyst; feed composition: 91.70% HCFO-1233zd(Z), 0.28% HCFO-1233zd(E), 7.99% HCFC-244fa, & 0.02% others; each temperature was run for at least 24 h; Productivity: 24.7 lb/hr/ft$^3$

EXAMPLE 3

Isomerization of HCFO-1233zd(Z)

A feed stream consisting of HCFO-1233zd(Z) was vaporized and reacted in the vapor phase over amorphous chromium oxyfluoride catalyst to produce HCFO-1233zd(E). Specifically, the feed material consisting of >99.50 GC area % HCFO-1233zd(Z) was vaporized and fed to a 1 inch reactor containing 0.28 L of amorphous chromium oxyfluoride pellets, at a rate of 0.6 lb/hr (272 g/hr), and reactor pressure of 50 psig. The reaction temperature was maintained between 220-230° C. The average productivity observed was 55.7 lb/hr (25.3 kg/hr) of HCFO-1233zd(E) per cubic foot (0.028 cubic meter) of amorphous chromium oxyfluoride catalyst. Table 3 shows average conversions of HCFO-1233zd(Z) and average selectivity to HCFO-1233zd (E) and byproducts, as a function of time on stream using amorphous chromium oxyfluoride catalyst.

TABLE 3

Average conversion of HCFO-1233zd(Z) and average selectivity to HCFO-1233zd(E) and byproducts using amorphous chromium oxyfluoride catalyst

| | Av. Conv % | Av. Selectivity % | | | | | | |
|---|---|---|---|---|---|---|---|---|
| Time, h | c-1233zd | t-1234ze | 245fa | c-1234ze | t-1233zd | 1232 | 243fa | others |
| 8 | 91.79 | 0.91 | 0.08 | 0.16 | 98.63 | 0.15 | 0.06 | 0.01 |
| 16 | 91.24 | 0.63 | 0.07 | 0.11 | 98.92 | 0.18 | 0.07 | 0.02 |
| 24 | 91.84 | 0.61 | 0.05 | 0.10 | 98.90 | 0.18 | 0.06 | 0.10 |
| 32 | 91.75 | 0.59 | 0.04 | 0.10 | 98.97 | 0.18 | 0.05 | 0.07 |
| 40 | 91.91 | 0.56 | 0.03 | 0.10 | 98.98 | 0.18 | 0.04 | 0.11 |

Feed composition: >99.5% c-1233zd; pressure 50 psig; amorphous chromium oxyfluoride; amount loaded 410 g; flow rate 0.6 lb/hr; reactor dimensions: 1" ID x 31" L; Productivity: 55.57 lb/h/ft$^3$

EXAMPLE 4

Dehydrohalogenation of HCFC-244fa

A feed stream consisting of HCFC-244fa was vaporized and reacted in the vapor phase over amorphous chromium oxyfluoride catalyst to produce HCFO-1233zd(E). Specifically, the feed material consisting of >99.50 GC area % HCFC-244fa was vaporized and fed to a 1 inch reactor containing 0.28 L of amorphous chromium oxyfluoride pellets, at a rate of 0.3 lb/hr (136 g/hr), and reactor pressure of 50 psig. The reaction temperature was maintained between 220-230° C. The average productivity observed was 18.2 lb/hr (8.3 kg/hr) of HCFO-1233zd(E) per cubic foot (0.028 cubic meter) of amorphous chromium oxyfluoride catalyst. Table 4 shows average conversions of HCFC-244fa, and average selectivity to HCFO-1233zd(E) and byproducts, as a function of time on stream using amorphous chromium oxyfluoride catalyst.

TABLE 4

Average conversion of HCFC-244fa and average selectivity to HCFO-1233zd(E) and byproducts using amorphous chromium oxyfluoride catalyst

| Time (h) | Avg. Conv. (%) 244fa | Avg. Selectivity (%) | | | | | | |
|---|---|---|---|---|---|---|---|---|
| | | t-1234ze | 245fa | c-1234ze | t-1233zd | c-1233zd | 243fa | Others |
| 2 | 97.13 | 1.64 | 29.49 | 0.23 | 61.02 | 5.24 | 1.61 | 0.77 |
| 4 | 97.46 | 1.85 | 29.01 | 0.28 | 60.57 | 5.45 | 1.27 | 1.56 |
| 6 | 96.76 | 2.07 | 30.02 | 0.32 | 60.06 | 5.35 | 1.21 | 0.98 |
| 8 | 97.76 | 1.92 | 29.40 | 0.28 | 61.35 | 5.05 | 1.03 | 0.97 |
| 10 | 93.66 | 2.12 | 30.14 | 0.34 | 60.26 | 5.71 | 1.26 | 0.17 |
| 12 | 83.77 | 2.14 | 29.81 | 0.42 | 58.43 | 7.17 | 1.77 | 0.25 |

Other conditions: 410 g of amorphous chromium oxyfluoride catalyst; feed composition: 99.5 wt % HCFC-244fa, 0.59 wt % HCFO-1233zd(Z), 0.1 wt % others; 220-230° C.; 50 psig; flow rate: 0.3 lb/hr, Productivity: 18.2 lb/h/ft$^3$.

EXAMPLE 5

Simultaneous Isomerization and Dehydrohalogenation in the Presence of HCFC-243fa or HCFC-243db, Using Amorphous Chromium Oxyfluoride Catalyst A feed stream consisting of HCFO-1233zd(Z), HCFC-244fa, HCFO-1233zd(E) and HCFC-243fa or HCFC-243db was vaporized and reacted in the vapor phase over amorphous chromium oxyfluoride catalyst to produce HCFO-1233zd(E). Specifically, the feed material consisting of about 91.72 GC area % HCFO-1233zd(Z), 6.55 GC area % HCFC-244fa, 0.07 GC area % HCFO-1233zd(E) and <3 GC area % HCFC-243fa or HCFC-243db was vaporized and fed to a 1 inch reactor containing 0.28 L of amorphous chromium oxyfluoride pellets, at a rate of 0.3 lb/hr (136 g/hr), and reactor pressure of 50 psig. The reaction temperature was maintained between 220-230° C. The average productivity observed was 54.5 lb/hr (24.7 kg/hr) of HCFO-1233zd(E) per cubic foot (0.028 cubic meter) of amorphous chromium oxyfluoride catalyst. Table 5 shows average conversions of HCFO-1233zd(Z), HCFC-244fa, HCFC-243fa, HCFC-243db and average selectivity to HCFO-1233zd(E) and byproducts, as a function of time on stream using amorphous chromium oxyfluoride catalyst.

TABLE 5

Average conversions of HCFO-1233zd(Z), HCFC-244fa, HCFC-243fa, HCFC-243db and average selectivity to HCFO-1233zd(E) and byproducts using amorphous chromium oxyfluoride catalyst

| Feed Composition (%) | | | | | |
|---|---|---|---|---|---|
| c-1233zd | t-1233zd | 244fa | 243fa | 243db | others |
| 92.96 | 0.06 | 6.96 | | | 0.001 |
| 90.98 | 0.07 | 6.36 | 2.10 | | 0.476 |
| 91.20 | 0.06 | 6.31 | | 2.25 | 0.164 |

| Average Conversion (%) | | | |
|---|---|---|---|
| c-1233zd | 244fa | 243fa | 243db |
| 92.79 | 96.98 | | |
| 92.70 | 95.26 | 89.06 | |
| 93.59 | 95.74 | | 74.83 |

| Average Selectivity (%) | |
|---|---|
| 1233xf | t-1233zd |
| UI | 95 73 |
| UI | 96.33 |
| 2.66 | 93 04 |

Other conditions: 225° C., 50 psig, 0.6 lb/h; time on stream for each feed mixture = 12 hrs; UI means unidentified; Productivity: 54.5 lb/h/ft$^3$.

The invention claimed is:

1. A method for simultaneous conversion of a mixture of HCFO-1233zd(Z) and HCFC-244fa to form HCFO-1233zd(E), comprising:
   providing a mixture including HCFO-1233zd(Z) and HCFC-244fa; and
   reacting the HCFO-1233zd(Z) and HCFC-244fa mixture in a vapor phase in the presence of a catalyst selected from the group consisting of chromium trifluoride ($CrF_3$), chromium oxide ($Cr_2O_3$), chromium oxyfluoride, aluminum fluoride, and combinations thereof to simultaneously isomerize HCFO-1233zd(Z) to form HCFO-1233zd(E) and dehydrohalogenate HCFC-244fa to form HCFO-1233zd(E),
   wherein said reacting step is conducted at a temperature between 80° C. and 275° C., and wherein said reacting step achieves a conversion of HCFO-1233zd(Z) to HCFO-1233zd(E) of 88% or greater.

2. The method of claim 1, wherein the catalyst comprises a catalyst selected from the group consisting of chromium trifluoride ($CrF_3$), chromium oxide ($Cr_2O_3$), and chromium oxyfluoride, and combinations thereof.

3. The method of claim 1, wherein said reacting step is conducted at a temperature between 80° C. and 170° C.

4. The method of claim 1, wherein said reacting step is conducted at a temperature between 100° C. and 275° C.

5. The method of claim 1, wherein a contact time between the composition and the catalyst is between 1 second and 150 seconds.

6. The method of claim 1, wherein a pressure in the reactor is between 0 psig and 100 psig.

7. The method of claim 1, wherein during the reacting step, the reactor includes less than 50 ppm water.

8. The method of claim 1, wherein in the providing step, total impurities are present in an amount less than 10 wt. %, based on the total weight of the composition.

9. The method of claim 1, wherein in the providing step, any compounds other than HCFO-1233zd(Z) and HCFC-244fa are present in an amount less than 6 wt. %, based on the total weight of the composition.

10. The method of claim 1, wherein in the providing step, any compounds other than HCFO-1233zd(Z) and HCFC-244fa are present in an amount less than 1.5 wt. %, based on the total weight of the composition.

11. The method of claim 1, wherein said reacting step achieves a conversion of HCFO-1233zd(Z) to HCFO-1233zd(E) between 88% and 96%, and wherein the catalyst is selected from the group consisting of chromium trifluoride ($CrF_3$), chromium oxide ($Cr_2O_3$), and chromium oxyfluoride and combinations thereof.

12. The method of claim 1, wherein said reacting step achieves a selectivity to HCFO-1233zd(E) between 90% and 97%, and wherein the catalyst is selected from the group consisting of chromium trifluoride ($CrF_3$) chromium oxide ($Cr_2O_3$), chromium oxyfluoride, and combinations thereof.

13. The method of claim 1, further comprising, after the reacting step, the additional steps of:
   distilling the composition in a distillation column;
   removing an overhead stream from the distillation column, the overhead stream concentrated in HCFO-1233zd(E); and
   removing a bottoms stream from the distillation column, the bottoms stream concentrated in HCFO-1233zd(Z) and HCFC-244fa.

14. The method of claim 13, further comprising, after the removing the bottoms stream step, the additional steps of:
   recycling the bottoms stream back to the reactor.

15. The method of claim 1, wherein the catalyst is an aluminum fluoride.

16. The method of claim 1, wherein said reacting step achieves a selectivity to HCFO-1233zd(E) 90% or greater.

* * * * *